(12) United States Patent
Eason et al.

(10) Patent No.: US 8,701,661 B2
(45) Date of Patent: Apr. 22, 2014

(54) INHALER

(75) Inventors: Stephen Eason, Cambridge (GB); Peter Evans, Cambridge (GB); Graham Gibbins, Cambridge (GB)

(73) Assignee: Vectura Delivery Devices Limited, Chippenham (GB)

( * ) Notice: Subject to any disclaimer, the term of this patent is extended or adjusted under 35 U.S.C. 154(b) by 654 days.

(21) Appl. No.: 12/864,154

(22) PCT Filed: Jan. 14, 2009

(86) PCT No.: PCT/EP2009/050344
§ 371 (c)(1),
(2), (4) Date: Oct. 14, 2010

(87) PCT Pub. No.: WO2009/092652
PCT Pub. Date: Jul. 30, 2009

(65) Prior Publication Data
US 2011/0030683 A1 Feb. 10, 2011

(30) Foreign Application Priority Data

Jan. 24, 2008 (EP) .................................... 08100892

(51) Int. Cl.
*A61M 15/00* (2006.01)
*A61M 16/00* (2006.01)
*B65D 83/16* (2006.01)

(52) U.S. Cl.
USPC ................................ 128/203.21; 128/203.12

(58) Field of Classification Search
USPC .......................... 128/200.14, 200.17, 200.21, 128/200.23–200.24, 203.12, 203.15, 128/203.21, 203.23, 204.18, 207.14; 221/25, 69–91
See application file for complete search history.

(56) References Cited

U.S. PATENT DOCUMENTS

2011/0132358 A1    6/2011    Eason et al.

FOREIGN PATENT DOCUMENTS

| JP | 5123399 | 3/2000 |
|----|---------|--------|
| JP | 2007533363 | 11/2007 |
| WO | WO 2005/037353 | 4/2005 |
| WO | WO 2006/123110 | 11/2006 |
| WO | WO 2007/012871 | 2/2007 |
| WO | WO 2007/096111 | 8/2007 |
| WO | WO 2007/134792 | 11/2007 |

OTHER PUBLICATIONS

The International Search Report issued in corresponding International Patent Application No. PCT/EP2009/050344.
Office Action dated Feb. 5, 2013, from the Japanese Patent Office concerning the corresponding Japanese Application No. 2010-543464.

*Primary Examiner* — Loan Thanh
*Assistant Examiner* — Joshua Lee
(74) *Attorney, Agent, or Firm* — Davidson, Davidson & Kappel, LLC

(57) ABSTRACT

An inhaler is disclosed. It comprises a housing to receive a strip having a plurality of blisters, each blister having a breachable lid and containing a dose of medicament for inhalation by a user, an indexing wheel mounted in the housing rotatable to drive a strip to sequentially move blisters into alignment with a blister piercing member, a control element pivotally mounted to the housing and a drive mechanism configured to couple the control element to the indexing wheel during part of the rotation of the control element by a user so that the indexing wheel rotates together with the control element.

26 Claims, 6 Drawing Sheets

INHALER

This application is a U.S. national phase application under U.S.C. §371 of International Application No. PCT/EP2009/050344, filed Jan. 14, 2009, which claims priority to European Patent Application No. EP08100892.2, filed Jan. 24, 2008, the disclosures of which are hereby incorporated by reference in their entirety.

The present invention relates to an inhalation device for oral or nasal delivery of medicament in powdered form. More specifically, the invention relates to an inhaler having a housing to receive a strip having a plurality of blisters spaced along the length of the strip, each blister having a puncturable lid and containing a dose of medicament for inhalation by a user. The invention also relates to an inhaler containing a strip of blisters each having a puncturable lid and containing a dose of medicament for inhalation by a user of the device according to the invention.

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in individual doses, usually in the form of capsules or blisters which each contain a single dose of the powder which has been accurately and consistently measured. A blister is generally cold formed from a ductile foil laminate or a plastics material and includes a puncturable lid which is permanently heat-sealed around the periphery of the blister during manufacture and after the dose has been introduced into the blister. A foil blister is preferred over capsules as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

Inhalation devices that receive a blister pack comprising a number of blisters each of which contain a pre-metered and individually packaged dose of the drug to be delivered are known. Actuation of the device causes a mechanism to breach or rupture a blister, such as by puncturing it or peeling the lid off, so that when the patient inhales, air is drawn through the blister entraining the dose therein that is then carried out of the blister through the device and via the patient's airway down into the lungs. Pressurized air or gas or other propellants may also be used to carry the dose out of the blister. Alternatively, the mechanism that punctures or opens the blister may push or eject the dose out of the blister into a receptacle from which the dose may subsequently be inhaled.

It is advantageous for the inhaler to be capable of holding a number of doses to enable it to be used repeatedly over a period of time without the requirement to open and/or insert a blister into the device each time it is used. Therefore, many conventional devices include means for storing a number of blisters each containing an individual dose of medicament. When a dose is to be inhaled, an indexing mechanism moves a previously emptied blister away from the opening mechanism so that a fresh one is moved into a position ready to be opened for inhalation of its contents.

An inhaler of the type described above is known from the Applicant's own co-pending international application no. PCT/GB2004/004416 filed on 18 Oct. 2004 and claiming priority from GB0324358.1 filed 17 Oct. 2003. This international application has been published as WO2005/037353 A1.

According to one embodiment described and claimed in WO 2005/037353 A1, and illustrated in FIGS. 1 and 2 of the accompanying drawings, an inhaler 1 has a housing 2 containing a coiled strip 3. The strip 3 has a plurality of individually spaced moisture proof blisters each containing a pre-measured dose of powdered medicament for inhalation. Each blister of the strip comprises a generally hemispherically shaped pocket and a flat puncturable lid permanently heat sealed to the pocket to hermetically seal the dose therein. The strip is preferably manufactured from foil laminate or a combination of foil laminate, such as aluminium, and plastics material.

An indexing mechanism 4 comprising a single actuating lever 5 unwinds the coil 3 one blister at a time so that they pass over a blister locating chassis 6 and successively through a blister piercing station 7, when the actuator 5 is pivoted in a direction indicated by arrow "A" in FIG. 2. The blister 3a located at the blister piercing station 7 on each movement of the actuator 5 is pierced on the return stroke of the actuator 5 (in the direction indicated by arrow "B" in FIG. 2) by piercing elements 8 on the actuator 5 itself so that, when a user inhales through a mouthpiece 9, an airflow is generated within the blister 3a to entrain the dose contained therein and carry it out of the blister 3a via the mouthpiece 9 and into the user's airway.

In another embodiment disclosed in WO2005/037353 A1, indexing and piercing of a blister positioned at the blister piercing station 7 is carried out in response to rotation of a cap that covers the mouthpiece in a closed position, rather than as a result of direct rotation of the actuator by the user.

Each of the devices disclosed in WO2005/037353 A1 have a drive mechanism that includes an indexing wheel. A blister strip passes over the indexing wheel and the wheel rotates in response to pivotal movement of an actuator or cap so as to drive or index the strip through the device. The drive mechanism is configured such that the indexing wheel rotates in response to rotation of the actuator or cap in one direction but remains stationary when the actuator or cap is rotated in the opposite direction.

The present invention seeks to provide an alternative an inhaler having an improved drive mechanism for coupling the actuator, or cap, to the indexing wheel so that rotation of the indexing wheel occurs during rotation of the cap or actuator in one direction. However, the invention also seeks to provide a modified drive mechanism in which the indexing wheel will rotate during only part of the movement of the actuator or cap in the same direction. In particular, the indexing wheel will rotate to index a strip during a first part of the movement of the actuator or cap in one direction and, when the actuator or cap has reached an intermediate position, the actuator or cap will disengage from the indexing wheel so that, during further movement of the actuator or cap in the same direction beyond the intermediate position, no further rotation of the indexing wheel will occur.

In a cap operated device in which a cap, which normally covers the mouthpiece in a closed position, is pivoted to index a strip and also to move an actuator to cause a piercing element mounted to or associated with the actuator to puncture the lid of a blister, the drive mechanism may be configured such that a fresh blister may be located in alignment with the blister piercing member when the intermediate position of the cap has been reached so that further movement of the cap in the same direction beyond the intermediate position causes the blister piercing member to pierce the pre-aligned and stationary blister.

According to the invention, there is provided an inhaler comprising a housing to receive a strip having a plurality of blisters, each blister having a breachable lid and containing a dose of medicament for inhalation by a user, an indexing wheel mounted in the housing rotatable to drive a strip to sequentially move blisters into alignment with a blister piercing member, a control element pivotally mounted to the housing and a drive mechanism configured to couple the control element to the indexing wheel during part of the rotation of the control element by a user so that the indexing wheel rotates together with the control element.

Preferably, the control element rotates relative to the housing about an axis and the drive mechanism comprises a coupling member in the housing for rotation about the same axis. Although the control element and coupling member preferably rotate about the same axis, it is also envisaged that they may rotate about separate axes that are offset from each other.

In a preferred embodiment, the control element and coupling member are connected so that they rotate together.

The indexing wheel may be rotatably mounted to the coupling member.

In a preferred embodiment, the coupling member includes a shaft having an axis coaxial with the axis of the control element, the indexing wheel being mounted on said shaft for rotation about said axis.

In one embodiment, the coupling member comprises an indexing wheel drive dog and the drive mechanism includes means to move, as the control element and coupling member are rotated, the indexing wheel drive dog into a position in which it cooperates with the indexing wheel so that the indexing wheel rotates together with the control element and the coupling member.

The coupling member is preferably formed from a resilient material and said means for moving the indexing wheel drive dog into a position in which it cooperates with the indexing wheel moves said indexing wheel drive dog against a bias provided by said resilience.

The coupling member may comprise a flange that extends radially from one end of the shaft across one end of the indexing wheel. Preferably, the flange lies in a plane extending substantially at right-angles to the axis of the shaft.

In one preferred embodiment, the flange includes a flexible flange portion that resiliently bends or flexes relative to the remaining portion of the flange about an axis extending substantially at right angles to the axis of the shaft.

The flange may have a cut-out region configured such that the flexible flange portion is joined only to the remaining portion of the flange to a limited extent.

In one embodiment, the flexible flange portion is hinged to the remaining portion of the flange at each end.

Conveniently, the indexing wheel drive dog upstands from a surface of the flexible flange portion in a direction towards the indexing wheel.

Preferably, the means to move the indexing wheel drive dog into a position in which it cooperates with the indexing wheel so that the indexing wheel rotates together with the control element comprises a coupling member deflecting dog protruding from the flexible flange portion.

In a preferred embodiment, the means to move the indexing wheel drive dog into a position in which it cooperates with the indexing wheel also comprises an arcuate guide track in the housing, the arcuate guide track having a first guide surface such that, when the coupling member is rotated in response to rotation of the control element in a first direction, the coupling member deflecting dog cooperates with the first guide surface to deflect the flexible flange portion towards the indexing wheel so that the indexing wheel drive dog cooperates with the indexing wheel to rotate the indexing wheel together with the coupling member.

The arcuate guide track is advantageously configured such that the coupling member deflecting dog drops off the first guide surface prior to rotation of the control element to its maximum extent, the resilience of the flexible flange portion causing it to return to its original undeflected state so that the indexing wheel drive dog no longer cooperates with the indexing wheel, the indexing wheel now remaining stationary during continued rotation of the control element and coupling member to its maximum extent.

The arcuate guide track preferably comprises a second guide surface such that, when the flange portion deflecting dog has dropped off the first guide surface and the coupling member is rotated in response to rotation of the control element in a reverse direction, the flange portion deflecting dog cooperates with said second guide surface so that the flexible flange portion is deflected in the opposite direction, away from the indexing wheel, so that the indexing wheel drive dog does not cooperate with the indexing wheel and the indexing wheel remains stationary.

The coupling member deflecting dog preferably comprises a first cooperating surface to engage the first guide surface of the arcuate guide track, and, a second cooperating surface to engage the second guide surface of the arcuate guide track.

The first and second guide surfaces of the arcuate guide track may extend parallel to each other but spaced from each other in an axial direction.

Ideally, the first and second guide surfaces have angled end regions such that the coupling member deflecting dog rides up the angled end regions onto respective guide surfaces.

In a preferred embodiment, the indexing wheel comprises a plurality of vanes and the indexing wheel drive dog contacts one of the vanes when the indexing wheel drive dog is moved into a position in which it cooperates with the indexing wheel so that the indexing wheel rotates together with the coupling member and the control element.

In a preferred embodiment, the inhaler comprises a locking element to prevent rotation of the indexing wheel other than during cooperation of the indexing wheel drive dog with the indexing wheel.

In this embodiment, the locking element preferably comprises a cantilevered arm mounted in the housing and having its free end biased against the indexing wheel, said free end of the cantilever arm cooperating with the indexing wheel so as to prevent rotation of the indexing wheel.

The free end of the cantilevered arm may be configured such that when the indexing wheel drive dog is moved towards the indexing wheel, further rotation of the coupling element causes the indexing wheel drive dog to engage the free end of the cantilever arm and deflect it out of locking engagement with the indexing wheel prior to cooperating with the indexing wheel to rotate the indexing wheel.

Preferably, the indexing wheel drive dog disengages the free end of the cantilever arm when the indexing wheel drive dog moves away from the indexing wheel so that the free end of the cantilever arm moves back towards the indexing wheel to lock the indexing wheel in position.

Preferably, the indexing wheel comprises a plurality of vanes and the free end of the cantilever arm comprises a slot, the slot being configured to receive a tip of a vane when the free end of the cantilever arm is biased against the indexing wheel to lock the indexing wheel in position.

Each vane may comprise an enlarged head portion and the slot in the free end of the cantilever arm is configured to receive said enlarged head portion.

Conveniently, the inhaler may comprise a chassis to locate a blister strip as it moves therethrough and the cantilever arm extends from said chassis.

According to another aspect, there is provided an inhaler according to the invention comprising a coiled strip of blisters received within the housing and passing around the indexing wheel.

Embodiments of the invention will now be described, by way of example only, with reference to FIGS. 3 to 8 of the accompanying drawings, in which:

FIGS. 1 and 2 are side views of a prior art inhalation device to show how a strip is driven to sequentially move blisters into alignment with a blister piercing element by movement of an actuator from the position shown in FIG. 1 to the position shown in FIG. 2 which drives an indexing wheel. A piercing head on the actuator pierces the lid of an aligned blister when the actuator is returned to its normal position, as shown in FIG. 1;

The drive mechanism of the present invention will now be described in detail with reference to FIGS. 3 to 8. It will be appreciated that this drive mechanism may be used in the inhaler described above with reference to FIGS. 1 and 2 but may also be used in other blister strip inhalation devices. In particular, it can also be used in a blister strip inhalation device in which a cap, which covers the mouthpiece in a closed position, is rotated to index the strip and in which an actuator is operable, either separately or in response to rotation of the cap to cause a blister piercing member to pierce the lid of an aligned blister. It may also be used in devices in which the used blisters are retained within the device. Therefore, although the following description primarily makes reference to an embodiment in which the actuator is rotated to index the strip, such as the actuator 5 of FIGS. 1 and 2, any control element is considered to fall within the scope of the invention, such as a "cap" that covers the mouthpiece and which is coupled to a separate actuator.

Figure 3:
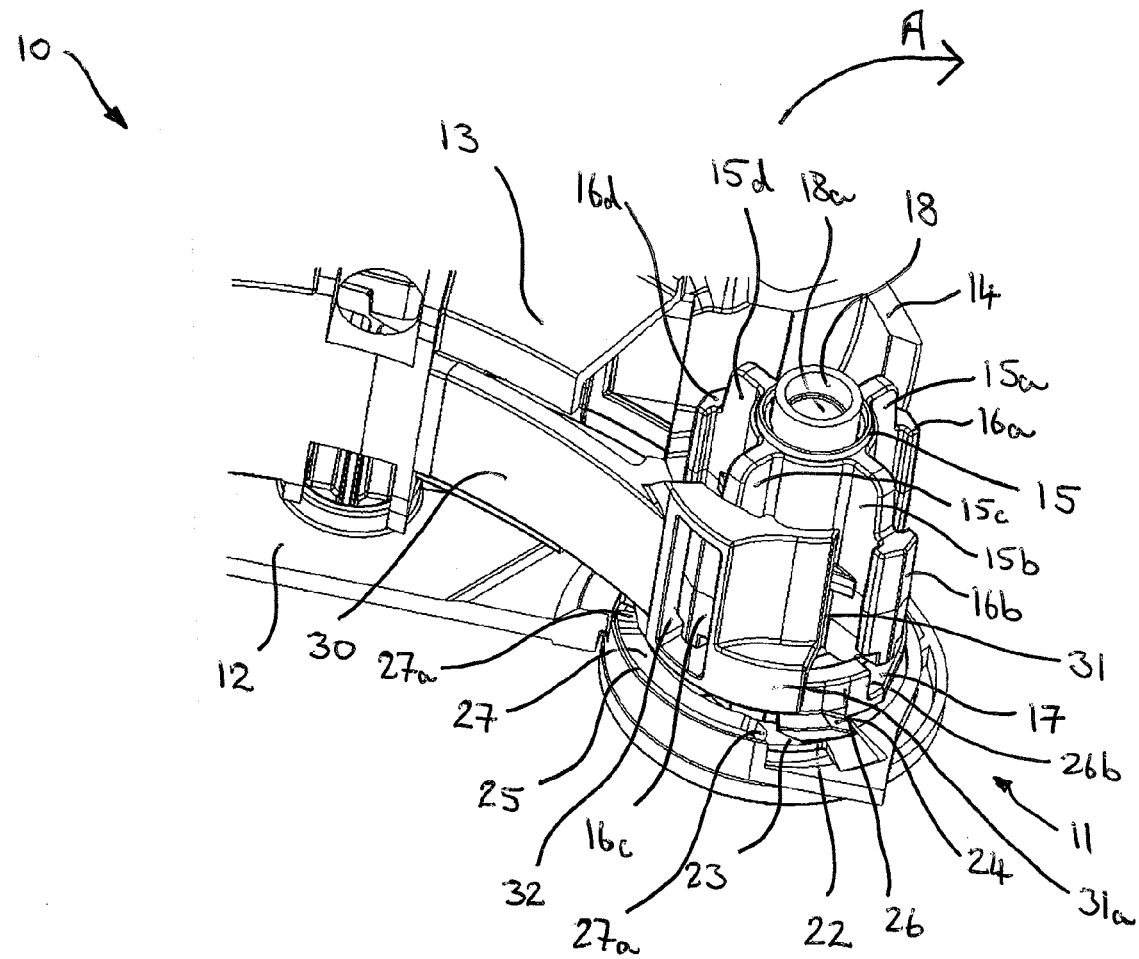
FIG. 3 is a partial perspective view of an inhaler according to the invention incorporating an improved blister strip indexing mechanism, with the actuator in its home, stowed or locked position prior to use of the inhaler.
Figure 4:
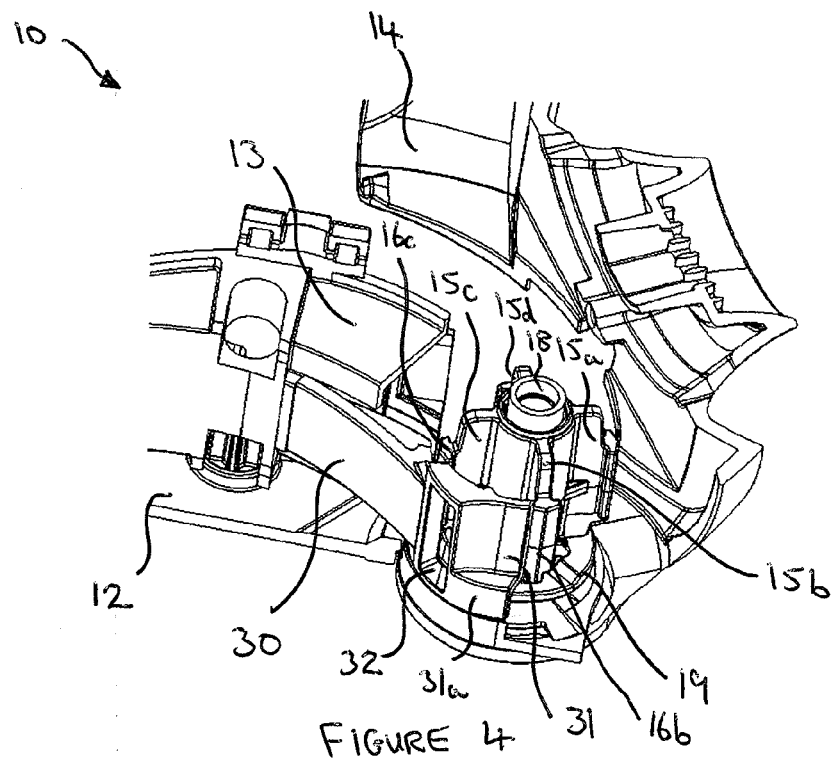
FIG. 4 is a partial perspective view of the inhaler shown in FIG. 3 in which the actuator has been rotated into an intermediate position from its home position.
Figure 5:
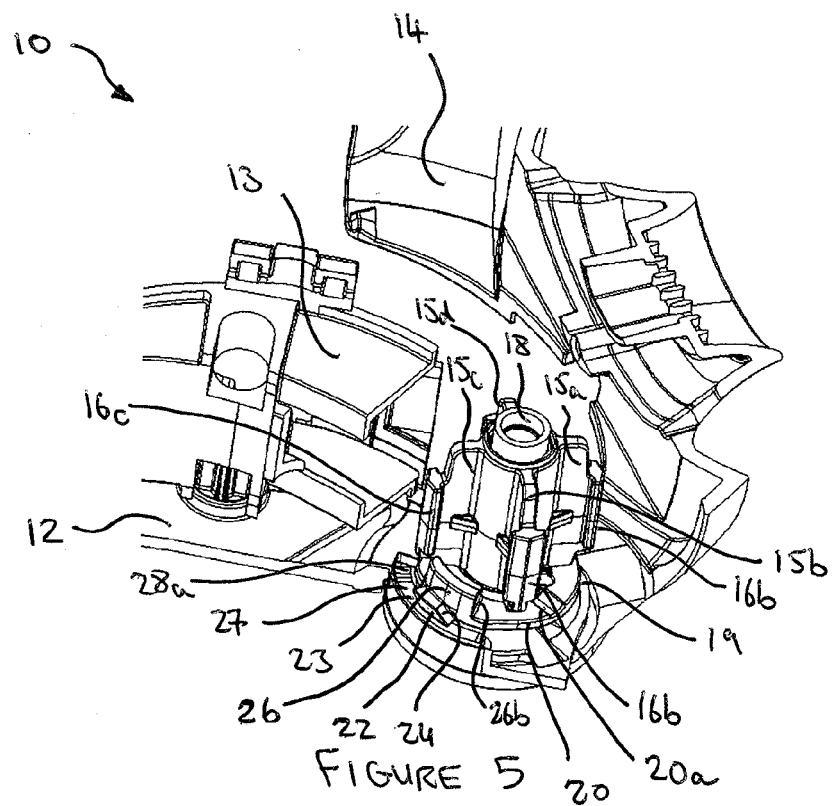
FIG. 5 is the same view as shown in FIG. 4, but with the cantilevered chassis arm omitted for clarity.
Figure 6:
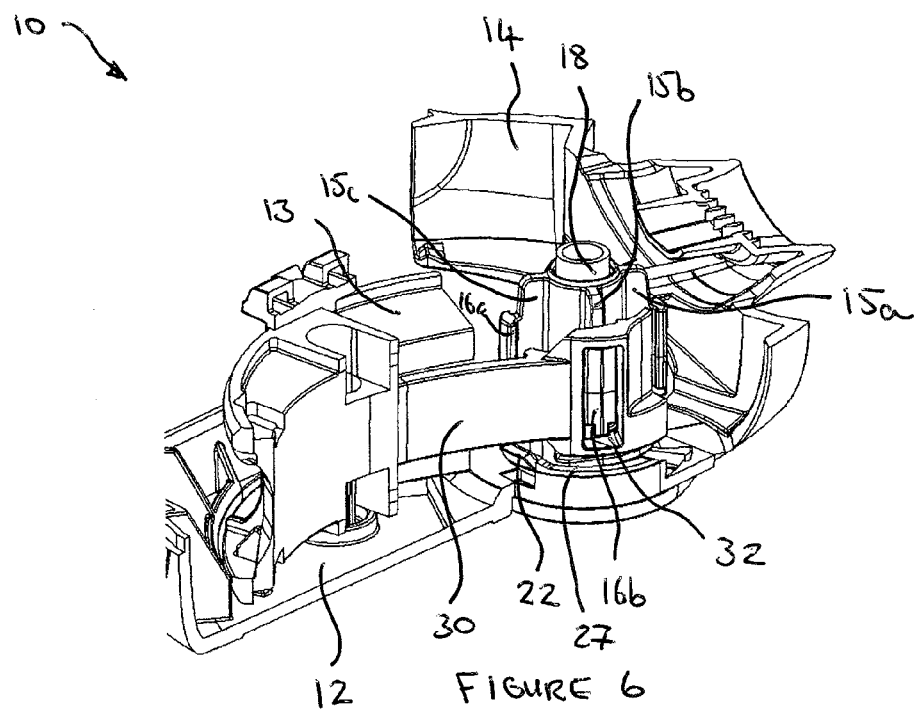
FIG. 6 is a partial perspective view of the inhaler shown in FIGS. 1 to 5, after the actuator has been rotated to a point at which drive between the drive coupling and the actuator has disengaged.
Figure 7:
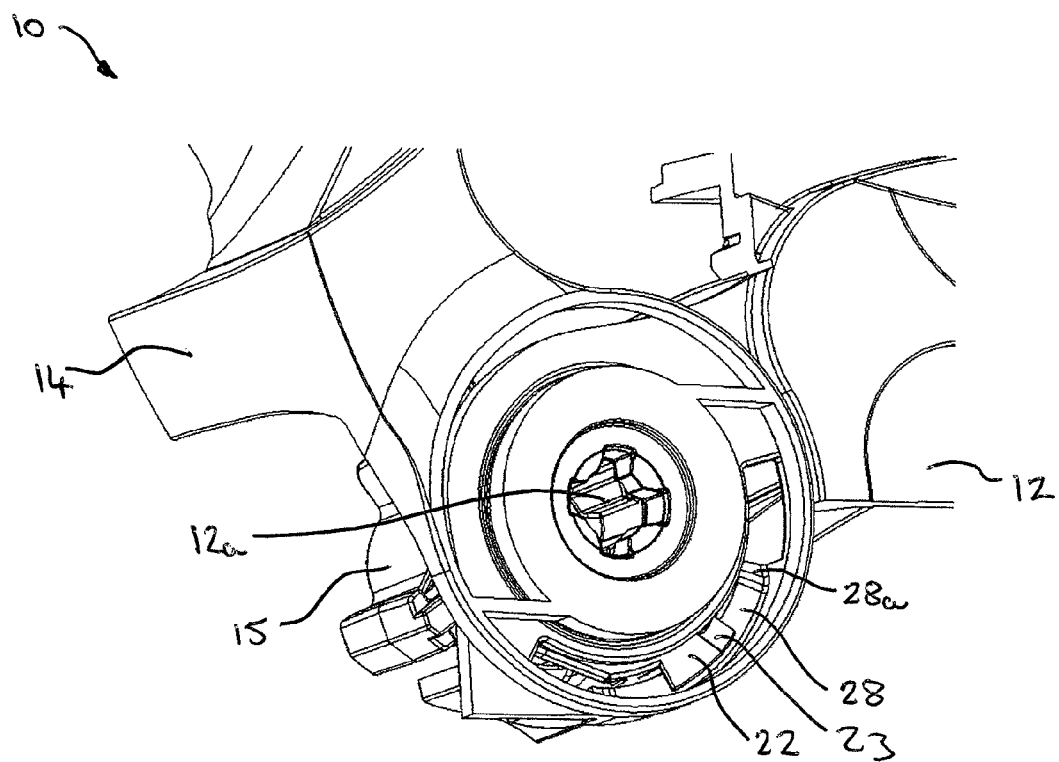
FIG. 7 is a partial perspective view of the opposite side of the inhaler shown in FIGS. 1 to 6.

Referring now to FIG. 3, there is shown a partial perspective view of an inhalation device 10 comprising an indexing mechanism 11 according to an embodiment of the present invention. It will be appreciated that parts of the housing 12 and internal components such as the blister locating chassis 13 and actuator 14 are only partially shown for the purposes of clarity and ease of understanding.

The indexing mechanism 11 includes an indexing wheel 15 comprising four vanes 15a,15b,15c,15d, each having an enlarged head portion 16a,16b,16c,16d. As is clear from reference to FIGS. 1 and 2, once a blister strip (not shown in FIGS. 3 to 8) has passed over the blister location chassis 13, it passes around the indexing wheel 15. A blister locates in the space between two vanes 15a,15b,15c,15d so that, as the indexing wheel 15 rotates in response to rotation of the actuator 14, a vane 15a,15b,15c,15d engages a blister located between the vanes 15a,15b,15c,15d so as to drive the strip around the indexing wheel 15 to sequentially move each blister forward by a sufficient distance to move a fresh blister into alignment with a blister piercing element (not shown in FIGS. 3 to 8).

The indexing mechanism 11 includes a drive coupling member 17 (most clearly shown in FIGS. 8a and 8b) for selectively or temporarily coupling the actuator 14 to the indexing wheel 15 so that, when coupled, the indexing wheel 15 rotates in response to rotation of the actuator 14 to index the strip. The drive coupling member 17 comprises a shaft 18 defining an axis of rotation "A" (see FIGS. 8a and 8b) on which the indexing wheel 15 is rotatably received so that it can rotate freely about the shaft 18 about said axis of rotation "A". The actuator 14 is fixedly attached to the drive coupling member 17 (such as by a splined pin—not shown)—that is inserted through the actuator 14, through an aperture 12a (see FIG. 7) in the housing 12 and is received within the opening 18a in the shaft 18) so that the drive coupling member 17 rotates together with the actuator 14 at all times. The actuator 14, drive coupling member 17 and indexing wheel 15 are all mounted coaxially for rotation about the same axis "A".

The drive coupling member 17 has a circular flange 19 that extends radially from one end of the shaft 18. A portion 20 of the flange is cut-away (see arcuate opening 21 in FIG. 8) over an angle of approximately 180 degrees where the flange 19 joins the shaft 18 so that this portion 20 of the flange 19 is not directly attached to the shaft 18 but only to the remaining portion of the flange 19 at each of its ends 20a,20b. As a result, this portion 20 of the flange 19 is flexible relative to the rest of the flange 19 and can be deflected out of the plane of the flange 19 that extends at right angles to the axis of the shaft, in an axial direction (indicated by "T" and "S", in FIG. 8 and FIG. 8b) either towards or away from the shaft 18 or, more importantly, towards or away from the indexing wheel 15 which is mounted on the shaft 18, when force is applied to it. This flexible flange portion 20 hinges about an axis B which intersects the axis A of the shaft 18 and actuator 14 but extends at right angles to it. The drive coupling member 17, or at least the flange 19, is made from a resilient material so that when the deflected flexible flange portion 20 is released, it returns to its neutral, unstressed position, in which it lies coplanar with the remaining fixed portion of the flange 19.

The flexible flange portion 20 has an integrally formed flange deflecting dog 22 projecting radially from its circumferential edge. The flange deflecting dog 22 has first and second angled engaging faces 23,24 on opposite sides. When the drive coupling member 17 is rotated in response to rotation of the actuator 14 in one direction, one of the first or second angled engaging faces 23,24 cooperate with a fixed formation 25 on the housing 12 to cause the flexible flange portion 20 to deflect in a first direction. When the drive coupling member 17 is rotated in the opposite direction, the other angled engaging face cooperates with the formation 25 on the housing 12 to cause the flexible flange portion 20 to deflect in a second, opposite direction, as will be explained in more detail below.

The flexible flange portion 20 also has an arcuately shaped indexing wheel drive dog 26 that upstands in an axial direction from its surface towards the indexing wheel 15 in the same direction as the shaft 18 and extends partially around the circumference of the flexible flange portion 20. As will now be explained in more detail below, an end face 26a (see FIG. 8a) of the indexing wheel drive dog 26 engages a vane 15a, 15b,15c,15d of the indexing wheel 15 when the flexible flange portion 20 has been deflected in a first direction, as indicated by arrow "T" in FIG. 8b (the flange portion 20 is shown in its deflected position in FIG. 8b), so that the indexing wheel 15 is driven together with the drive coupling member 17.

As mentioned above, the flange deflecting dog 22 engages a formation 25 on the housing 12 when the drive coupling member rotates in response to rotation of the actuator 14 so as to flex the deflectable portion 20 of the flange 19. This formation 25 comprises first and second arcuately shaped tracks or paths 27, 28 positioned one above the other or spaced from each other in the axial direction. The surface of the innermost track 27 is visible in FIG. 1. The lower or outermost track 28 is located beneath it and is visible in FIG. 7. The ends of the tracks 27a, 28a have angled faces for reasons that will become apparent.

When the actuator 14 is rotated in a first direction (the direction indicated by arrow "A" in FIG. 3), the drive coupling member 17 rotates together with it and the first outwardly facing angled surface 23 on the flange deflecting dog 22 contacts the angled face 27a of the innermost track 27. Further rotation of the drive coupling member 17 causes the flange deflecting dog 22 to ride up onto the surface of the innermost track 27 thereby deflecting the flexible flange portion 20 inwardly, i.e. in a direction into the housing 12 or towards the shaft 18 and the indexing wheel 15 and the direction indicated by arrow "T" in FIG. 8b.

Figure 1:
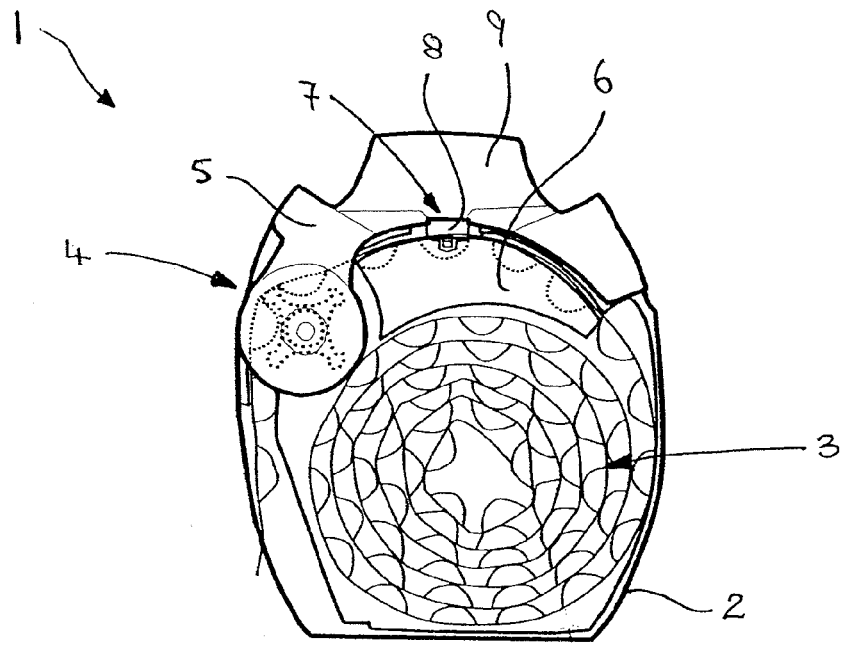
Figure 2:
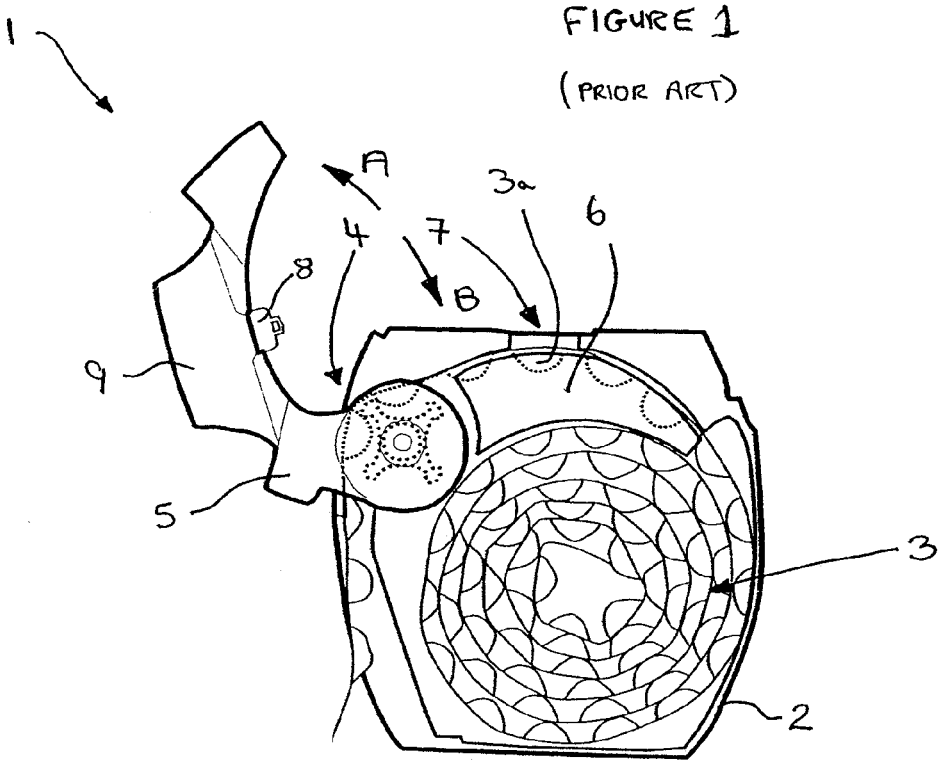

When the flexible flange portion 20 has been deflected inwardly in the direction of arrow T, further rotation of the drive coupling member 17 causes the indexing wheel drive dog 26 to engage a vane, which as shown in FIG. 1 is vane 15c, of the indexing wheel 15 so that the indexing wheel 15 rotates together with the drive coupling member 17 and drive to the indexing wheel 15 is engaged.

When the end of the innermost track 27 has been reached, the flange deflecting dog 22 falls off the surface of the track 27 and the resilience of the flexible flange portion 20 causes it to return to its original unstressed or neutral position. When the drive coupling member 17 is rotated further, the indexing wheel drive dog 26 no longer engages with the vane 15c of the indexing wheel 15 and instead passes beneath it so the indexing wheel 15 remains stationary. Therefore, drive to the indexing wheel 15 is disengaged, despite continued rotation of the actuator 14 in the same direction.

Figure 8A:
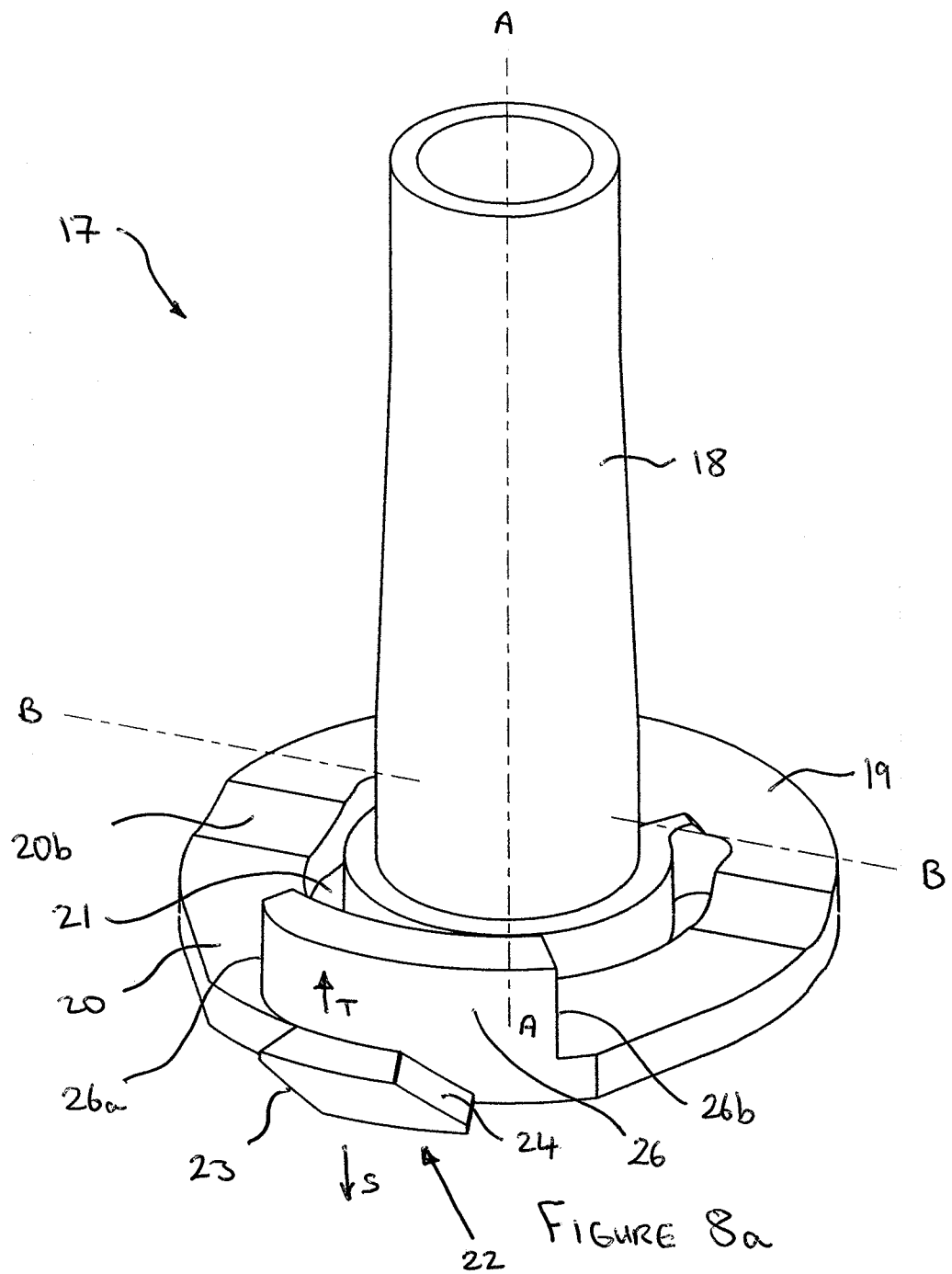
FIG. 8a is a perspective view of the drive coupling used in the indexing mechanism of the inhalers shown in FIGS. 1 to 7.
Figure 8B:
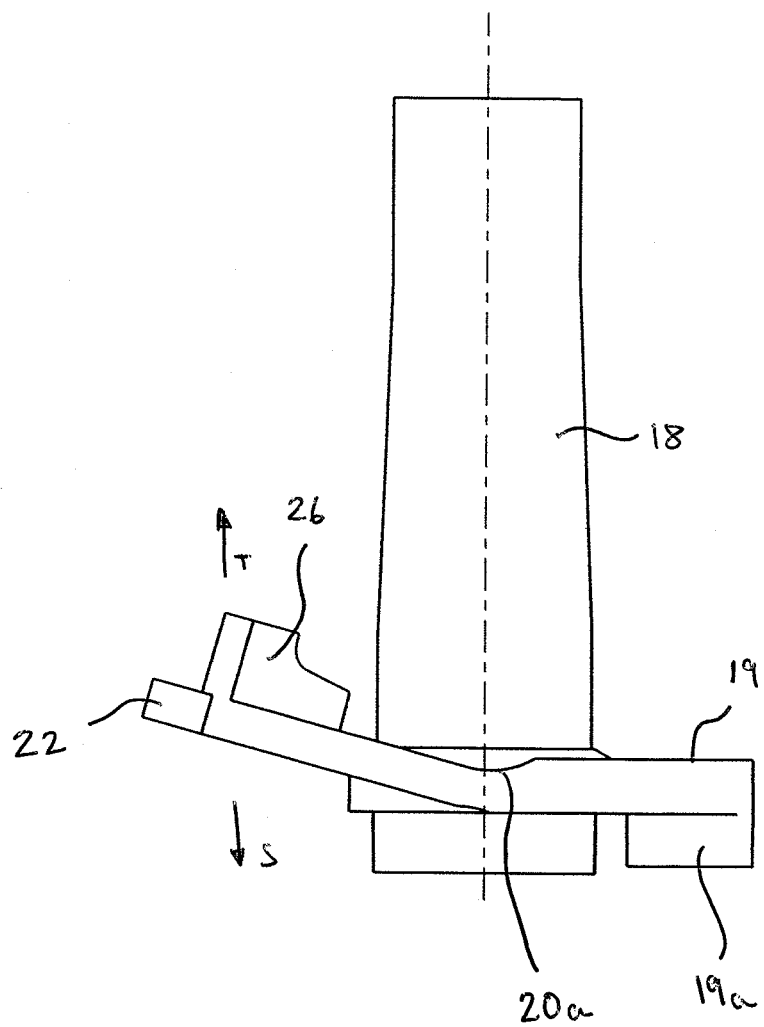
FIG. 8b is a side view of the drive coupling illustrated in FIG. 8a in which the flexible flange portion has been deflected in a direction "T" towards the shaft or, towards an indexing wheel mounted on that shaft.

When the actuator 14 is rotated back in the opposite direction towards its home position, the second inwardly facing angled surface 24 of the flange deflecting dog 22 now contacts the lower or outermost track 28 so that the flange deflecting dog 22 now rides onto the surface of that second track 28, thereby causing the flexible flange portion 20 to deflect outwardly or in the opposite direction to the direction in which it was previously deflected, i.e in the direction indicated by arrow marked "S" in FIG. 8b. Engagement of the flange deflecting dog 22 with the outermost track 28 so as to deflect the flange portion 20 in the opposite direction, enables the drive coupling member 17 to rotate in the opposite direction without any drive to the indexing wheel 15. It will be appreciated that, if the flange portion 20 was not deflected in the opposite direction, the flange deflecting dog 22 would simply engage against the end of the formation 25 in the housing 12 when rotated back in the opposite direction, thereby preventing rotation in the opposite direction or, the flange deflecting dog 22 would travel back over the innermost track 27 deflecting the flexible flange portion 20 in the same direction causing the opposite end 26b of the indexing wheel drive dog 26 to engage with a vane 15b of the indexing wheel 15 thereby driving the indexing wheel 15 backwards rather than leaving it stationary with no drive engaged. Therefore, it is necessary to ensure that the flexible flange portion 20 is deflected in the opposite direction, i.e. in the direction of arrow "S" in FIG. 8a, so that there is no drive to the indexing wheel during rotation of the coupling member 17 in the opposite direction.

When the drive deflecting dog 22 reaches the end of the outermost track 28, the flexible flange portion 20 returns to its original unstressed or neutral position, due to its resilience.

In a preferred embodiment, the indexing mechanism 11 also includes means for locking the indexing wheel 15 to prevent its rotation between indexing steps and means for temporarily releasing that lock to allow rotation of the indexing wheel 15 when driven by the indexing wheel drive dog 26. The lock also improves positional accuracy of the strip and, more specifically, the next blister to be pierced. This locking arrangement will now be described in more detail below.

The blister location chassis 13 comprises a resiliently flexible cantilever arm 30 that extends from the body 13 of the chassis towards the indexing wheel 15. The free end of the cantilever arm 30 has an enlarged head portion 31 comprising a letterbox shaped slot, window or opening 32 in which the head 16c of a vane 15c of the indexing wheel 15 is located. The opening 32 is dimensioned such that the head 16c of the vane 15c (as shown in FIG. 1) is a snug fit therein so that rotation of the indexing wheel 15 is prevented. In the normal or home position of the actuator 14, the head 16c of a vane 15c is located in said opening 32 in the cantilever arm 30 of the chassis 13 so that rotation of the indexing wheel 15 is prevented.

When the actuator 14 is rotated and the flange drive dog 22 engages the innermost track 27 so as to deflect the flexible portion of the flange 20 inwardly towards the indexing wheel 15, the indexing wheel drive dog 26 initially engages with a protrusion 31a from the enlarged head 31 on the cantilever arm 30 of the chassis 13 so that the cantilever arm 30 is deflected outwardly, away from the indexing wheel 15, to free the head 16c of the vane 15c from the slot 32, thereby unlocking the indexing wheel 15. Only once the indexing wheel 15 has been released by the indexing wheel drive dog 26 pushing the cantilever arm 30 away from the indexing wheel 15 does the indexing wheel drive dog 26 subsequently engage a vane 15c of the indexing wheel 15 so that further rotation of the drive coupling member 17 rotates the indexing wheel 15.

Prior to the flange drive dog 22 falling off the end of the innermost track 28 and the flexible flange portion 20 returning to its undeflected state due to its resilience, the indexing wheel drive dog 26 no longer pushes against the cantilever arm 30 and so the cantilever arm 30 is free to move back towards the indexing wheel 15. As the cantilever arm 30 is free to move back just prior to rotation of the indexing wheel 15 being completed, the cantilever arm is prevented from moving all the way back by the head 16b of a following vane 15b which contacts the cantilever arm 30. During further rotation of the indexing wheel, the head 16b slides across the cantilever arm and then drops into the opening 32 thereby allowing the cantilever arm 30 to move all the way back and locking the indexing wheel 15 in position prior to any further rotation of the drive coupling member 17 in response to continued rotation of the actuator 14.

On the return stroke of the actuator 14, it will be appreciated that deflection of the flexible flange portion 20 in the opposite direction, i.e. in a direction away from the indexing wheel and in the direction indicated by arrow "S" in FIG. 8b, also ensures that the indexing wheel drive dog 26 clears the chassis arm 30 and so the indexing wheel 15 is not unlocked, thereby preventing any rotation of the indexing wheel 15 during the return stroke.

It will be appreciated that the extent of rotation of the indexing wheel 15 relative to the extent of rotation of the actuator 14 may be controlled by altering the circumferential length of the inner and outer tracks 27,28. If the tracks are made longer, the flexible flange portion 20 will be deflected for a greater proportion of the angle through which the actuator 14 is rotated and so the indexing wheel drive dog 26 will be engaged with the indexing wheel 15 to rotate the indexing wheel 15 throughout that angle. If required, the tracks 27,28 could be made sufficiently long so that the indexing wheel 15 rotates during rotation of the actuator 14 through its entire angle of movement in one direction. Alternatively, the tracks 27,28 could be made shorter to reduce the angle through which the actuator 14 and indexing wheel 15 rotate together. Ideally, the track length can be selected so that the indexing wheel 15 is rotated through a sufficient angle to move the next, unused blister, into alignment with the blister piercing element, any further rotation of the actuator 14 can either be lost motion, i.e. it performs no function or some other function. For example, if it is the cap that is rotated, this last period of rotation of the cap can operate a separate actuator to cause it to pierce the lid of said blister that has just been moved into alignment with the blister piercing element.

It will be appreciated that the indexing mechanism 11 is designed to enable a stroke to be aborted when the actuator 14 or cap has been rotated through an angle which is sufficient to cause initial indexing of the strip but which is not such that the drive to the indexing wheel 15 has disengaged, i.e. a position in which the flange drive dog 22 has not reached the end of the innermost track 27. If the stroke is aborted and the actuator 14 returned to its rest position before drive to the indexing wheel 15 has disengaged, the strip will be driven backwards into its original position as a rear surface 26b of the indexing wheel drive dog 26 will engage a preceding vane 15b to drive the indexing wheel 15 in the opposite direction. It will be appreciated that this has the advantage that the user may partially open the actuator 14 to enable them to inspect and/or clean a mouthpiece and then close it again without having indexed the strip or pierced a blister.

The flange 19 is provided with a downwardly depending lug 19a (see FIG. 8b) that engages with a feature (not shown) on the casework when the actuator or cap has reached its fully open extent, thereby preventing any further rotation of the actuator or cap.

A variety of medicaments may be administered alone by using inhalers of the invention. Specific active agents or drugs that may be used include, but are not limited to, agents of one or more of the following classes listed below.

1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, mitodrine, naphazoline, norepinephrine, oxymetazoline, pemoline, phenylephrine, phenylethylamine, phenylpropanolamine, pirbuterol, prenalterol, procaterol, propylhexedrine, pseudoephedrine, ritodrine, salbutamol, salmeterol, terbutaline, tetrahydrozoline, tramazoline, tyramine and xylometazoline.

2) Adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol, sotalol, tamsulosin, terazosin, timolol, tolazoline, trimazosin, urapidil and yohimbine.

3) Adrenergic neurone blockers such as, for example, bethanidine, debrisoquine, guabenxan, guanadrel, guanazodine, guanethidine, guanoclor and guanoxan.

4) Drugs for treatment of addiction, such as, for example, buprenorphine.

5) Drugs for treatment of alcoholism, such as, for example, disulfuram, naloxone and naltrexone.

6) Drugs for Alzheimer's disease management, including acetylcholinesterase inhibitors such as, for example, donepezil, galantamine, rivastigmine and tacrin.

7) Anaesthetics such as, for example amethocaine, benzocaine, bupivacaine, hydrocortisone, ketamine, lignocaine, methylprednisolone, prilocaine, proxymetacaine, ropivacaine and tyrothricin.

8) Angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril.

9) Angiotensin II receptor blockers, such as, for example, candesartan, cilexetil, eprosartan, irbesartan, losartan, medoxomil, olmesartan, telmisartan and valsartan.

10) Antiarrhythmics such as, for example, adenosine, amidodarone, disopyramide, flecainide acetate, lidocaine hydrochloride, mexiletine, procainamide, propafenone and quinidine.

11) Antibiotic and antibacterial agents (including the betalactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan.

12) Anti-clotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin.

13) Anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenyloin; phenyltriazines including lamotrigine; and miscellaneous anticonvulsants including acetazolamide, carbamazepine, ethosuximide, fosphenyloin, gabapentin, levetiracetam, oxcarbazepine, piracetam, pregabalin, primidone, sodium valproate, topiramate, valproic acid and zonisamide.

14) Antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIs) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, α-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine, cotinine, fezolamine, flupentixol, idazoxan, kitanserin, levoprotiline, lithium salts, maprotiline, medifoxamine, methylphenidate, metralindole, minaprine, nefazodone, nisoxetine, nomifensine, oxaflozane, oxitriptan, phenyhydrazine, rolipram, roxindole, sibutramine, teniloxazine, tianeptine, tofenacin, trazadone, tryptophan, viloxazine and zalospirone.

15) Anticholinergic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium.

16) Antidiabetic agents such as, for example, pioglitazone, rosiglitazone and troglitazone.

17) Antidotes such as, for example, deferoxamine, edrophonium chloride, fiumazenil, nalmefene, naloxone, and naltrexone.

18) Anti-emetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron.

19) Antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine.

20) Anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; beta-lactams including cefazolin, cefmetazole, cefoperazone, cefoxitin, cephacetrile, cephalexin, cephaloglycin and cephaloridine; cephalosporins, including cephalosporin C and cephalothin; cephamycins such as cephamycin A, cephamycin B, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin O, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole.

21) Anti-neoplastic agents such as, for example, droloxifene, tamoxifen and toremifene.

22) Antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galanthamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone.

23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides.

24) Antirheumatic agents such as, for example, diclofenac, heparinoid, hydroxychloroquine and methotrexate, leflunomide and teriflunomide.

25) Anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, zolpidem and zopiclone.

26) Appetite stimulants such as, for example, dronabinol.

27) Appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents.

28) Benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam.

29) Bisphosphonates such as, for example, alendronate sodium, sodium clodronate, etidronate disodium, ibandronic acid, pamidronate disodium, isedronate sodium, tiludronic acid and zoledronic acid.

30) Blood modifiers such as, for example, cilostazol and dipyridamol, and blood factors.

31) Cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocamide, torsemide, triamterene, valsartan and verapamil.

32) Calcium channel blockers such as, for example, amlodipine, bepridil, diltiazem, felodipine, flunarizine, gallopamil, isradipine, lacidipine, lercanidipine, nicardipine, nifedipine, nimodipine and verapamil.

33) Central nervous system stimulants such as, for example, amphetamine, brucine, caffeine, dexfenfluramine, dextroamphetamine, ephedrine, fenfluramine, mazindol, methylphenidate, modafinil, pemoline, phentermine and sibutramine.

34) Cholesterol-lowering drugs such as, for example, acipimox, atorvastatin, ciprofibrate, colestipol, colestyramine, bezafibrate, ezetimibe, fenofibrate, fluvastatin, gemfibrozil, ispaghula, nictotinic acid, omega-3 triglycerides, pravastatin, rosuvastatin and simvastatin.

35) Drugs for cystic fibrosis management such as, for example, *Pseudomonas aeruginosa* infection vaccines (eg Aerugen™), alpha 1-antitripsin, amikacin, cefadroxil, denufosol, duramycin, glutathione, mannitol, and tobramycin.

36) Diagnostic agents such as, for example, adenosine and aminohippuric acid.

37) Dietary supplements such as, for example, melatonin and vitamins including vitamin E.

38) Diuretics such as, for example, amiloride, bendroflumethiazide, bumetanide, chlortalidone, cyclopenthiazide, furosemide, indapamide, metolazone, spironolactone and torasemide.

39) Dopamine agonists such as, for example, amantadine, apomorphine, bromocriptine, cabergoline, lisuride, pergolide, pramipexole and ropinerole.

40) Drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine.

41) Gastrointestinal agents such as, for example, atropine, hyoscyamine, famotidine, lansoprazole, loperamide, omeprazole and rebeprazole.

42) Hormones and analogues such as, for example, cortisone, epinephrine, estradiol, insulin, Ostabolin-C, parathyroid hormone and testosterone.

43) Hormonal drugs such as, for example, desmopressin, lanreotide, leuprolide, octreotide, pegvisomant, protirelin, salcotonin, somatropin, tetracosactide, thyroxine and vasopressin.

44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose.

45) Immunoglobulins.

46) Immunomodulators such as, for example, interferon (e.g. interferon beta-1a and interferon beta-1b) and glatiramer.

47) Immunosupressives such as, for example, azathioprine, cyclosporin, mycophenolic acid, rapamycin, sirolimus and tacrolimus.

48) Mast cell stabilizers such as, for example, cromoglycate, iodoxamide, nedocromil, ketotifen, tryptase inhibitors and pemirolast.

49) Drugs for treatment of migraine headaches such as, for example, almotriptan, alperopride, amitriptyline, amoxapine, atenolol, clonidine, codeine, coproxamol, cyproheptadine, dextropropoxypene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and non-steroidal anti-inflammatory drugs.

50) Drugs for treatment of motion sickness such as, for example, diphenhydramine, promethazine and scopolamine.

51) Mucolytic agents such as N-acetylcysteine, ambroxol, amiloride, dextrans, heparin, desulphated heparin, low molecular weight heparin and recombinant human DNase.

52) Drugs for multiple sclerosis management such as, for example, bencyclane, methylprednisolone, mitoxantrone and prednisolone.

53) Muscle relaxants such as, for example, baclofen, chlorzoxazone, cyclobenzaprine, methocarbamol, orphenadrine, quinine and tizanidine.

54) NMDA receptor antagonists such as, for example, mementine.

55) Nonsteroidal anti-inflammatory agents such as, for example, aceclofenac, acetaminophen, alminoprofen, amfenac, aminopropylon, amixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib.

56) Nucleic-acid medicines such as, for example, oligonucleotides, decoy nucleotides, antisense nucleotides and other gene-based medicine molecules.

57) Opiates and opioids such as, for example, alfentanil, allylprodine, alphaprodine, anileridine, benzylmorphine, bezitramide, buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papavereturn, pentazocine, pethidine, phenazocine, pholcodeine, remifentanil, sufentanil, tramadol, and combinations thereof with an anti-emetic.

58) Opthalmic preparations such as, for example, betaxolol and ketotifen.

59) Osteoporosis preparations such as, for example, alendronate, estradiol, estropitate, raloxifene and risedronate.

60) Other analgesics such as, for example, apazone, benzpiperylon, benzydamine, caffeine, cannabinoids, clonixin, ethoheptazine, flupirtine, nefopam, orphenadrine, pentazocine, propacetamol and propoxyphene.

61) Other anti-inflammatory agents such as, for example, B-cell inhibitors, p38 MAP kinase inhibitors and TNF inhibitors.

62) Phosphodiesterase inhibitors such as, for example, non-specific phosphodiesterase inhibitors including theophylline, theobromine, IBMX, pentoxifylline and papaverine; phosphodiesterase type 3 inhibitors including bipyridines such as milrinone, aminone and olprinone; imidazolones such as piroximone and enoximone; imidazolines such as imazodan and 5-methyl-imazodan; imidazoquinoxalines; and dihydropyridazinones such as indolidan and LY181512 (5-(6-oxo-1,4,5,6-tetrahydro-pyridazin-3-yl)-1,3-dihydro-indol-2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ONO 6126, tolafentrine and zardaverine, and including quinazolinediones such as nitraquazone and nitraquazone analogs; xanthine derivatives such as denbufylline and arofylline; tetrahydropyrimidones such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N-(2-pyrimidinylmethyl) carbamoyl]pyrimidine, 2-(5,6,7,8-tetrahydro-1,7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl) carbamoyl]-pyrimidine).

63) Potassium channel modulators such as, for example, cromakalim, diazoxide, glibenclamide, levcromakalim, minoxidil, nicorandil and pinacidil.

64) Prostaglandins such as, for example, alprostadil, dinoprostone, epoprostanol and misoprostol.

65) Respiratory agents and agents for the treatment of respiratory diseases including bronchodilators such as, for example, the $\beta_2$-agonists bambuterol, bitolterol, broxaterol, carmoterol, clenbuterol, fenoterol, formoterol, indacaterol, levalbuterol, metaproterenol, orciprenaline, picumeterol, pirbuterol, procaterol, reproterol, rimiterol, salbutamol, salmeterol, terbutaline and the like; inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotrine receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton.

66) Sedatives and hypnotics such as, for example, alprazolam, butalbital, chlordiazepoxide, diazepam, estazolam, flunitrazepam, flurazepam, lorazepam, midazolam, temazepam, triazolam, zaleplon, zolpidem, and zopiclone.

67) Serotonin agonists such as, for example, 1-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline, ipsaperone, lysergic acid diethylamide, 2-methyl serotonin, mezacopride, sumatriptan, tiaspirone, trazodone and zacopride.

68) Serotonin antagonists such as, for example, amitryptiline, azatadine, chlorpromazine, clozapine, cyproheptadine, dexfenfluramine, R(+)-α-(2,3-dimethoxyphenyl)-1-[2-(4-fluorophenyl)ethyl]-4-piperidine-methanol, dolasetron, fenclonine, fenfluramine, granisetron, ketanserin, methysergide, metoclopramide, mianserin, ondansetron, risperidone, ritanserin, trimethobenzamide and tropisetron.

69) Steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neomycin sulphate, prednisolone, rimexolone, rofleponide, triamcinolone and triamcinolone acetonide.

70) Sympathomimetic drugs such as, for example, adrenaline, dexamfetamine, dipirefin, dobutamine, dopamine, dopexamine, isoprenaline, noradrenaline, phenylephrine, pseudoephedrine, tramazoline and xylometazoline.

71) Nitrates such as, for example, glyceryl trinitrate, isosorbide dinitrate and isosorbide mononitrate.

72) Skin and mucous membrane agents such as, for example, bergapten, isotretinoin and methoxsalen.

73) Smoking cessation aids such as, for example, bupropion, nicotine and varenicline.

74) Drugs for treatment of Tourette's syndrome such as, for example, pimozide.

75) Drugs for treatment of urinary tract infections such as, for example, darifenicin, oxybutynin, propantheline bromide and tolteridine.

76) Vaccines.

77) Drugs for treating vertigo such as, for example, betahistine and meclizine.

78) Therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, and protamine zinc insulin.

79) Anticancer agents such as, for example, anthracyclines, doxorubicin, idarubicin, epirubicin, methotrexate, taxanes, paclitaxel, docetaxel, cisplatin, vinca alkaloids, vincristine and 5-fluorouracil.

80) Pharmaceutically acceptable salts or derivatives of any of the foregoing.

It should be noted that drugs listed above under a particular indication or class may also find utility in other indications. A plurality of active agents can be employed in the practice of the present invention. An inhaler according to the invention may also be used to deliver combinations of two or more different active agents or drugs. Specific combinations of two medicaments which may be mentioned include combinations of steroids and $\beta_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and formoterol; ciclesonide and salmeterol; mometasone and formoterol; and mometasone and salmeterol. Specifically, inhalers according to the invention may also be used to deliver combinations of three different active agents or drugs.

It will be clear to a person of skill in the art that, where appropriate, the active agents or drugs may be linked to a carrier molecule or molecules and/or used in the form of prodrugs, salts, as esters, or as solvates to optimise the activity and/or stability of the active agent or drug.

Anticholinergic agents are referred to above (see No. 15). It is also envisaged that the pharmaceutical composition may comprise one or more, preferably one, anticholinergic 1, optionally in combination with a pharmaceutically acceptable excipient.

The anticholinergic 1 can be selected from the group consisting of
a) tiotropium salts 1a,
b) compounds of formula 1c

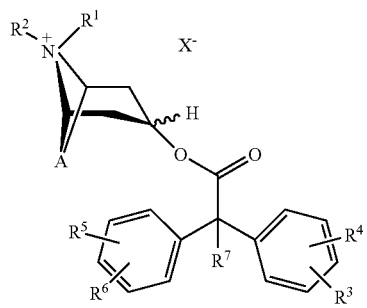

1c wherein
A denotes a double-bonded group selected from among

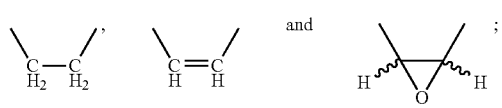

$X^-$ denotes an anion with a single negative charge, preferably an anion selected from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate,
$R^1$ and $R^2$ which may be identical or different denote a group selected from among methyl, ethyl, n-propyl and iso-propyl, which may optionally be substituted by hydroxy or fluorine, preferably unsubstituted methyl;

$R^3$, $R^4$, $R^5$ and $R^6$, which may be identical or different, denote hydrogen, methyl, ethyl, methyloxy, ethyloxy, hydroxy, fluorine, chlorine, bromine, CN, $CF_3$ or $NO_2$;

$R^7$ denotes hydrogen, methyl, ethyl, methyloxy, ethyloxy, —$CH_2$—F, —$CH_2$—$CH_2$—F, -O-$CH_2$—F, -O-$CH_2$—$CH_2$—F, —$CH_2$—OH, —$CH_2$—$CH_2$—OH, $CF_3$, —$CH_2$—OMe, —$CH_2$—$CH_2$—OMe, —$CH_2$—OEt, —$CH_2$—$CH_2$—OEt, —O—COMe, —O—COEt, -Q-COCF$_3$, -Q-COCF$_3$, fluorine, chlorine or bromine;

c) compounds of formula 1d

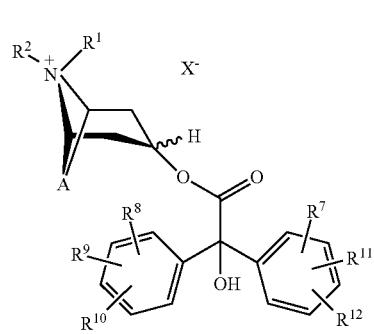

1d wherein
A, $X^-$, $R^1$ and $R^2$ may have the meanings as mentioned hereinbefore and wherein $R^7$, $R^8$, $R^9$, $R^{10}$, $R^{11}$ and $R^{12}$, which may be identical or different, denote hydrogen, methyl, ethyl, methyloxy, ethyloxy, hydroxy, fluorine, chlorine, bromine, CN, $CF_3$ or $NO_2$, with the proviso that at least one of the groups $R^7$, $R^8$, $R^9$, $R^{10}$, $R^{11}$ and $R^{12}$ is not hydrogen, d) compounds of formula 1e

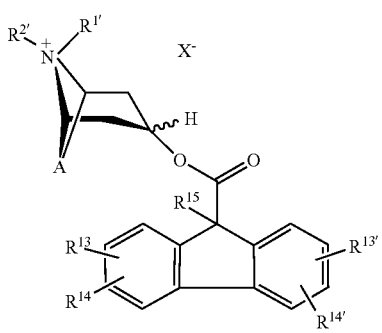

1e wherein A and $X^-$ may have the meanings as mentioned hereinbefore, and wherein $R^{15}$ denotes hydrogen, hydroxy, methyl, ethyl, —$CF_3$, $CHF_2$ or fluorine;

$R^{1'}$ and $R^{2'}$ which may be identical or different denote $C_1$-$C_5$-alkyl which may optionally be substituted by $C_3$-$C_6$-cycloalkyl, hydroxy or halogen, or $R^{1'}$ and $R2'$ together denote a —$C_3$-$C_5$-alkylene-bridge;

$R^{13}$, $R^{14}$, $R^{13'}$ and $R^{14'}$ which may be identical or different denote hydrogen, —$C_1$-$C_4$-alkyl, —$C_1$-$C_4$-alkyloxy, hydroxy, —$CF_3$, —$CHF_2$, CN, $NO_2$ or halogen, e) compounds of formula 1f

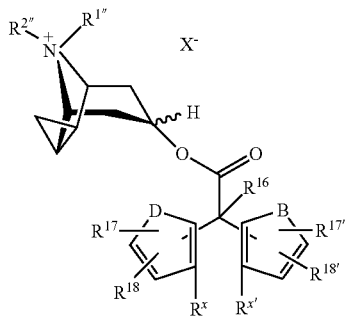

1f wherein X⁻ may have the meanings as mentioned hereinbefore, and wherein

D and B which may be identical or different, preferably identical, denote —O—, —S—, —NH—, —CH$_2$—, —CH=CH—, or —N(C$_1$-C$_4$-alkyl)-;

$R^{16}$ denotes hydrogen, hydroxy, —C$_1$-C$_4$-alkyl, —C$_1$-C$_4$-alkyloxy, —C$_1$-C$_4$-alkylene-Halogen, —O—C$_1$-C$_4$ alkylene-halogen, —C$_1$-C$_4$-alkylene-OH, —CF$_3$, CHF$_2$, —C$_1$-C$_4$-alkylene-C$_1$-C$_4$ alkyloxy, —O—COC$_1$-C$_4$-alkyl, —O—COC$_1$-C$_4$-alkylene-halogen, —C$_1$-C$_4$-alkylene-C$_3$-C$_6$-cycloalkyl, —O—COCF$_3$ or halogen;

$R^{1\prime\prime}$ and $R^{2\prime\prime}$ which may be identical or different, denote —C$_1$-C$_5$-alkyl, which may optionally be substituted by —C$_3$-C$_6$-cycloalkyl, hydroxy or halogen, or $R^{1\prime\prime}$ and $R^{2\prime\prime}$ together denote a —C3-C5-alkylene bridge;

$R^{17}$, $R^{18}$, $R^{17\prime}$ and $R^{18\prime}$, which may be identical or different, denote hydrogen, C$_1$-C$_4$-alkyl, C$_1$-C$_4$-alkyloxy, hydroxy, —CF$_3$, —CHF$_2$, CN, NO$_2$ or halogen;

$R^x$ and $R^{x\prime}$ which may be identical or different, denote hydrogen, C$_1$-C$_4$-alkyl, C$_1$-C$_4$-alkyloxy, hydroxy, —CF$_3$, —CHF$_2$, CN, NO$_2$ or halogen or $R^x$ and $R^{x\prime}$ together denote a single bond or a bridging group selected from among the bridges —O—, —S—, —NH—, —CH$_2$—, —CH$_2$—CH$_2$—, —N(C$_1$-C$_4$-alkyl)-, —CH(C$_1$-C$_4$-alkyl)- and —C(C$_1$-C$_4$-alkyl)$_2$, and f) compounds of formula 1g

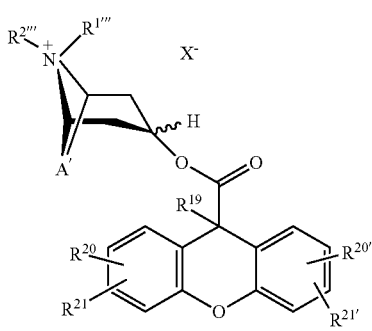

1g wherein X⁻ may have the meanings as mentioned hereinbefore, and wherein A' denotes a double-bonded group selected from among

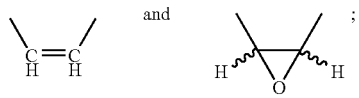

$R^{19}$ denotes hydroxy, methyl, hydroxymethyl, ethyl, —CF$_3$, CHF$_2$ or fluorine;

$R^{1\prime\prime\prime}$ and $R^{2\prime\prime\prime}$ which may be identical or different denote C$_1$-C$_5$-alkyl which may optionally be substituted by C$_3$-C$_6$-cycloalkyl, hydroxy or halogen, or $R^{1\prime\prime\prime}$ and $R^{2\prime\prime\prime}$ together denote a —C$_3$-C$_5$-alkylene-bridge;

$R^{20}$, $R^{21}$, $R^{20\prime}$ and $R^{21\prime}$ which may be identical or different denote hydrogen, —C$_1$-C$_4$-alkyl, —C$_1$-C$_4$-alkyloxy, hydroxy, —CF$_3$, —CHF$_2$, CN, NO$_2$ or halogen.

The compounds of formula 1c are known in the art (WO 02/32899).

In a preferred embodiment of the invention the method comprises administration of compounds of formula 1c, wherein X⁻ denotes bromide;

$R^1$ and $R^2$ which may be identical or different denote a group selected from methyl and ethyl, preferably methyl;

$R^3$, $R^4$, $R^5$ and $R^6$, which may be identical or different, denote hydrogen, methyl, methyloxy, chlorine or fluorine;

$R^7$ denotes hydrogen, methyl or fluorine, optionally together with a pharmaceutically acceptable excipient.

Of particular importance are compounds of general formula 1c, wherein A denotes a double-bonded group selected from among

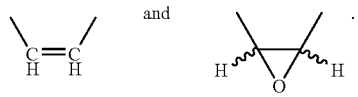

The compounds of formula 1c, may optionally be administered in the form of the individual optical isomers, mixtures of the individual enantiomers or racemates thereof.

Of particular importance within a method according to the invention are the following compounds of formula 1c:
tropenol 2,2-diphenylpropionic acid ester methobromide,
scopine 2,2-diphenylpropionic acid ester methobromide,
scopine 2-fluoro-2,2-diphenylacetic acid ester methobromide and
tropenol 2-fluoro-2,2-diphenylacetic acid ester methobromide.

The compounds of formula 1d are known in the art (WO 02/32898).

In a preferred embodiment of the invention the method comprises administration of compounds of formula 1d, wherein A denotes a double-bonded group selected from among

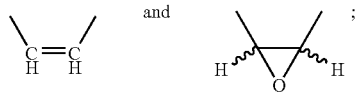

X⁻ denotes bromide;

$R^1$ and $R^2$ which may be identical or different denote methyl or ethyl, preferably methyl;

$R^7$, $R^8$, $R^9$, $R^{10}$, $R^{11}$ and $R^{12}$, which may be identical or different, denote hydrogen, fluorine, chlorine or bromine, preferably fluorine with the proviso that at least one of the groups $R^7$, $R^8$, $R^9$, $R^{10}$, $R^{11}$ and $R^{12}$ not hydrogen, optionally together with a pharmaceutically acceptable excipient.

Of particular importance within the method according to the invention are the following compounds of formula 1d:
tropenol 3,3',4,4'-tetrafluorobenzilic acid ester methobromide,
scopine 3,3',4,4'-tetrafluorobenzilic acid ester methobromide,
scopine 4,4'-difluorobenzilic acid ester methobromide,
tropenol 4,4'-difluorobenzilic acid ester methobromide,
scopine 3,3'-difluorobenzilic acid ester methobromide, and
tropenol 3,3'-difluorobenzilic acid ester methobromide.

The pharmaceutical compositions according to the invention may contain the compounds of formula 1d optionally in the form of the individual optical isomers, mixtures of the individual enantiomers or racemates thereof.

The compounds of formula 1e are known in the art (WO 03/064419).

In a preferred embodiment of the invention the method comprises administration of compounds of formula 1e, wherein
A denotes a double-bonded group selected from among

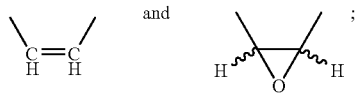

$X^-$ denotes an anion selected from among chloride, bromide and methanesulphonate, preferably bromide;
$R^{15}$ denotes hydroxy, methyl or fluorine, preferably methyl or hydroxy;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen, $-CF_3$, $-CHF_2$ or fluorine, preferably hydrogen or fluorine, optionally together with a pharmaceutically acceptable excipient.

In another preferred embodiment of the invention the method comprises administration of compounds of formula 1e, wherein
A denotes a double-bonded group selected from among

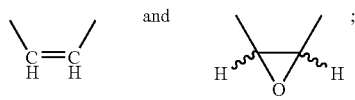

$X^-$ denotes bromide;
$R^{15}$ denotes hydroxy or methyl, preferably methyl;
$R^{1'}$ and $R^{2'}$ which may be identical or different represent methyl or ethyl, preferably methyl;
$R^{13}$, $R^{14}$, $R^{13'}$ and $R^{14'}$ which may be identical or different represent hydrogen or fluorine, optionally together with a pharmaceutically acceptable excipient.

Of particular importance within the method according to the invention are the following compounds of formula 1e:
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide.

The pharmaceutical compositions according to the invention may contain the compounds of formula 1e optionally in the form of the individual optical isomers, mixtures of the individual enantiomers or racemates thereof.

The compounds of formula 1f are known in the art (WO 03/064418).

In another preferred embodiment of the invention the method comprises administration of compounds of formula 1f wherein
$X^-$ denotes chloride, bromide, or methanesulphonate, preferably bromide;
D and B which may be identical or different, preferably identical, denote $-O-$, $-S-$, $-NH-$ or $-CH=CH-$;
$R^{16}$ denotes hydrogen, hydroxy, $-C_1$-$C_4$-alkyl, $-C_1$-$C_4$alkyloxy, $-CF_3$, $-CHF_2$, fluorine, chlorine or bromine;
$R^{1''}$ and $R^{2''}$ which may be identical or different, denote $C_1$-$C_4$-alky, which may optionally be substituted by hydroxy, fluorine, chlorine or bromine, or
$R^{1''}$ and $R^{2''}$ together denote a $-C_3$-$C_4$-alkylene-bridge;
$R^{17}$, $R^{18}$, $R^{17'}$ and $R^{18'}$, which may be identical or different, denote hydrogen, $C_1$-$C_4$-alkyl, $C_1$-$C_4$-alkyloxy, hydroxy, $-CF_3$, $-CHF_2$, CN, $NO_2$, fluorine, chlorine or bromine;
$R^x$ and $R^{x'}$ which may be identical or different, denote hydrogen, $C_1$-$C_4$-alkyl, $C_1$-$C_4$-alkyloxy, hydroxy, $-CF_3$, $-CHF_2$, CN, $NO_2$, fluorine, chlorine or bromine or
$R^x$ and $R^{x'}$ together denote a single bond or a bridging group selected from among the bridges $-O-$, $-S-$, $-NH-$ and $-CH_2-$, optionally together with a pharmaceutically acceptable excipient.

In another preferred embodiment of the invention the method comprises administration of compounds of formula 1f, wherein
$X^-$ denotes chloride, bromide, or methanesulphonate, preferably bromide;
D and B which may be identical or different, preferably identical, denote $-S-$ or $-CH=CH-$;
$R^{16}$ denotes hydrogen, hydroxy or methyl;
$R^{1''}$ and $R^{2''}$ which may be identical or different, denote methyl or ethyl;
$R^{17}$, $R^{18}$, $R^{17'}$ and $R^{18'}$, which may be identical or different, denote hydrogen, $-CF_3$ or fluorine, preferably hydrogen;
$R^x$ and $R^{x'}$ which may be identical or different, denote hydrogen, $-CF_3$ or fluorine, preferably hydrogen or
$R^x$ and $R^{x'}$ together denote a single bond or the bridging group $-O-$, optionally together with a pharmaceutically acceptable excipient.

In another preferred embodiment of the invention the method comprises administration of compounds of formula 1f wherein denotes bromide;
$X^-$ denotes bromide;
D and B denote $-CH=CH-$;
$R^{16}$ denotes hydrogen, hydroxy or methyl;
$R^{1''}$ and $R^{2''}$ denote methyl;
$R^{17}$, $R^{18}$, $R^{17'}$ and $R^{18'}$, which may be identical or different, denote hydrogen or fluorine, preferably hydrogen;
$R^x$ and $R^{x'}$ which may be identical or different, denote hydrogen or fluorine, preferably hydrogen or
$R^x$ and $R^{x'}$ together denote a single bond or the bridging group $-O-$, optionally together with a pharmaceutically acceptable excipient.

Of particular importance within the method according to the invention are the following compounds of formula 1f:
cyclopropyltropine benzilate methobromide; cyclopropyltropine 2,2-diphenylpropionate methobromide; cyclopropyltropine 9-hydroxy-xanthene-9-carboxylate methobromide; cyclopropyltropine 9-methyl-fluorene-9-carboxylate methobromide; cyclopropyltropine 9-methyl-xanthene-9-carboxylate methobromide; cyclopropyltropine 9-hydroxy-fluorene-9-carboxylate methobromide; cyclopropyltropine methyl 4,4'-difluorobenzilate methobromide.

The pharmaceutical compositions according to the invention may contain the compounds of formula 1f optionally in the form of the individual optical isomers, mixtures of the individual enantiomers or racemates thereof.

The compounds of formula 1g are known in the art (WO 03/064417).

In another preferred embodiment of the invention the method comprises administration of compounds of formula 1g wherein
A' denotes a double-bonded group selected from among

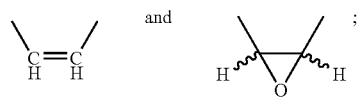

X⁻ denotes chloride, bromide or methanesulphonate, preferably bromide;
$R^{19}$ denotes hydroxy or methyl;
$R^{1'''}$ and $R^{2'''}$ which may be identical or different represent methyl or ethyl, preferably methyl;
$R^{20}$, $R^{21}$, $R^{20'}$ and $R^{21'}$ which may be identical or different represent hydrogen, —CF₃, —CHF₂ or fluorine, preferably hydrogen or fluorine, optionally together with a pharmaceutically acceptable excipient.

In another preferred embodiment of the invention the method comprises administration of compounds of formula 1g wherein
A' denotes a double-bonded group selected from among

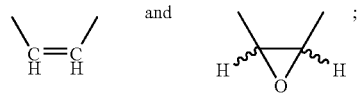

X⁻ denotes bromide;
$R^{19}$ denotes hydroxy or methyl, preferably methyl;
$R^{1'''}$ and $R^{2'''}$ which may be identical or different represent methyl or ethyl, preferably methyl;
$R^3$, $R^4$, $R^{3'}$ and $R^{4'}$ which may be identical or different represent hydrogen or fluorine, optionally together with a pharmaceutically acceptable excipient.

Of particular importance within the method according to the invention are the following compounds of formula 1g:
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide.

The pharmaceutical compositions according to the invention may contain the compounds of formula 1g optionally in the form of the individual optical isomers, mixtures of the individual enantiomers or racemates thereof.

The alkyl groups used, unless otherwise stated, are branched and unbranched alkyl groups having 1 to 5 carbon atoms. Examples include: methyl, ethyl, propyl or butyl. The groups methyl, ethyl, propyl or butyl may optionally also be referred to by the abbreviations Me, Et, Prop or Bu. Unless otherwise stated, the definitions propyl and butyl also include all possible isomeric forms of the groups in question. Thus, for example, propyl includes n-propyl and iso-propyl, butyl includes iso-butyl, sec. butyl and tert.-butyl, etc.

The cycloalkyl groups used, unless otherwise stated, are alicyclic groups with 3 to 6 carbon atoms. These are the cyclopropyl, cyclobutyl, cyclopentyl and cyclohexyl groups. According to the invention cyclopropyl is of particular importance within the scope of the present invention.

The alkylene groups used, unless otherwise stated, are branched and unbranched double-bonded alkyl bridges with 1 to 5 carbon atoms. Examples include: methylene, ethylene, propylene or butylene.

The alkylene-halogen groups used, unless otherwise stated, are branched and unbranched double-bonded alkyl bridges with 1 to 4 carbon atoms which may be mono-, di- or trisubstituted, preferably disubstituted, by a halogen. Accordingly, unless otherwise stated, the term alkylene-OH groups denotes branched and unbranched double-bonded alkyl bridges with 1 to 4 carbon atoms which may be mono-, di- or trisubstituted, preferably monosubstituted, by a hydroxy.

The alkyloxy groups used, unless otherwise stated, are branched and unbranched alkyl groups with 1 to 5 carbon atoms which are linked via an oxygen atom. The following may be mentioned, for example: methyloxy, ethyloxy, propyloxy or butyloxy. The groups methyloxy, ethyloxy, propyloxy or butyloxy may optionally also be referred to by the abbreviations MeO, EtO, PropO or BuO. Unless otherwise stated, the definitions propyloxy and butyloxy also include all possible isomeric forms of the groups in question. Thus, for example, propyloxy includes n-propyloxy and iso-propyloxy, butyloxy includes iso-butyloxy, sec. butyloxy and tert.-butyloxy, etc. The word alkoxy may also possibly be used within the scope of the present invention instead of the word alkyloxy. The groups methyloxy, ethyloxy, propyloxy or butyloxy may optionally also be referred to as methoxy, ethoxy, propoxy or butoxy.

The alkylene-alkyloxy groups used, unless otherwise stated, are branched and unbranched double-bonded alkyl bridges with 1 to 5 carbon atoms which may be mono-, di- or trisubstituted, preferably monosubstituted, by an alkyloxy group.

The —O—CO-alkyl groups used, unless otherwise stated, are branched and unbranched alkyl groups with 1 to 4 carbon atoms which are bonded via an ester group. The alkyl groups are bonded directly to the carbonylcarbon of the ester group. The term —O—CO-alkyl-halogen group should be understood analogously. The group —O—CO—CF₃ denotes trifluoroacetate.

Within the scope of the present invention halogen denotes fluorine, chlorine, bromine or iodine. Unless otherwise stated, fluorine and bromine are the preferred halogens. The group CO denotes a carbonyl group.

The inhalation device according to the invention comprises the compounds of formula 1 preferably in admixture with a pharmaceutically acceptable excipient to form a powder mixture. The following pharmaceutically acceptable excipients may be used to prepare these inhalable powder mixtures according to the invention: monosaccharides (e.g. glucose or arabinose), disaccharides (e.g. lactose, saccharose, maltose, trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose and trehalose are the particularly preferred excipients, while lactose, preferably in form of its monohydrate is most particularly preferred.

The compounds of formula 1 may be used in the form of their racemates, enantiomers or mixtures thereof. The separation of enantiomers from the racemates may be carried out using methods known in the art (e.g. by chromatography on chiral phases, etc.).

Optionally, the inhalation device according to the invention contains plural of doses of a medicament in powder form that contains, beside one compound of formula 1, another active ingredient.

Preferably the additional active ingredient is a beta$_2$ agonists 2 which is selected from the group consisting of albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-0X0-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

According to the instant invention more preferred beta$_2$ agonists 2 are selected from the group consisting of bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-0X0-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluormethylphenyl)-2-tert.-butylamino)ethanol and 1-(4-ethoxycarbonylamino-3-cyano-5-fluorophenyl)-2-(tert.-butylamino)ethanol, optionally in the form of the racemates, the enantiomers, the diastereomers and optionally the pharmacologically acceptable acid addition salts and the hydrates thereof.

More preferably, the betamimetics 2 used as within the compositions according to the invention are selected from among fenoterol, formoterol, salmeterol, 3-(4-{6-[2-Hydroxy-2-(4-hydroxy-3-hydroxymethyl-phenyl)-ethylamino]-hexyloxy}-butyl)-benzenesulfoneamide, 5-[2-(5,6-Diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, the enantiomers, the diastereomers and optionally the pharmacologically acceptable acid addition salts thereof, and the hydrates thereof. Of the betamimetics mentioned above the compounds formoterol, salmeterol, 3-(4-{6-[2-Hydroxy-2-(4-hydroxy-3-hydroxymethyl-phenyl)-ethylamino]-hexyloxy}-butyl)-benzenesulfoneamide, and 5-[2-(5,6-Diethyl-indan-2-ylamino)-1-hydroxy-ethyl]-8-hydroxy-1H-quinolin-2-one are particularly preferred, optionally in the form of the racemates, the enantiomers, the diastereomers and optionally the pharmacologically acceptable acid addition salts thereof, and the hydrates thereof. Of the betamimetics mentioned above the compounds formoterol and salmeterol are particularly preferred, optionally in the form of the racemates, the enantiomers, the diastereomers and optionally the pharmacologically acceptable acid addition salts thereof, and the hydrates thereof.

Examples of pharmacologically acceptable acid addition salts of the betamimetics 2 according to the invention are the pharmaceutically acceptable salts which are selected from among the salts of hydrochloric acid, hydrobromic acid, sulphuric acid, phosphoric acid, methanesulphonic acid, acetic acid, fumaric acid, succinic acid, lactic acid, citric acid, tartaric acid, 1-hydroxy-2-naphthalenecarboxylic acid, 4-phenylcinnamic acid, 5-(2,4-difluorophenyl)salicylic acid or maleic acid. If desired, mixtures of the abovementioned acids may also be used to prepare the salts 2.

According to the invention, the salts of the betamimetics 2 selected from among the hydrochloride, hydrobromide, sulphate, phosphate, fumarate, methanesulphonate, 4-phenylcinnamate, 5-(2,4-difluorophenyl)salicylate, maleate and xinafoate are preferred. Particularly preferred are the salts of 2 in the case of salmeterol selected from among the hydrochloride, sulphate, 4-phenylcinnamate, 5-(2,4-difluorophenyl)salicylate and xinafoate, of which the 4-phenylcinnamate, 5-(2,4-difluorophenyl)salicylate and especially xinafoate are particularly important. Particularly preferred are the salts of 2 in the case of formoterol selected from the hydrochloride, sulphate and fumarate, of which the hydrochloride and fumarate are particularly preferred, such as formoterol fumarate.

Salts of salmeterol, formoterol, 3-(4-{6-[2-Hydroxy-2-(4-hydroxy-3-hydroxymethyl-phenyl)-ethylamino]-hexyloxy}- butyl)-benzenesulfoneamide, and 5-[2-(5,6-Diethyl-indan-2-ylamino)-1-hydroxy-ethyl]-8-hydroxy-1H-quinolin-2-one, are preferably used as the betamimetics 2 according to the invention. Of particular importance are salmeterol and formoterol salts. Any reference to the term betamimetics 2 also includes a reference to the relevant enantiomers or mixtures thereof. In the pharmaceutical compositions according to the invention, the compounds 2 may be present in the form of their racemates, enantiomers or mixtures thereof. The separation of the enantiomers from the racemates may be carried out using methods known in the art (e.g. by chromatography on chiral phases, etc.) If the compounds 2 are used in the form of their enantiomers, it is particularly preferable to use the enantiomers in the R configuration at the C—OH group.

Optionally, the inhalation device according to the invention contains plural of doses of a medicament in powder form that contains beside one compound of formula 1 a steroid 3 as another active ingredient.

In such medicament combinations the steroid 3 is preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (5)-fluoromethyl 6α,9α-difluoro-17α-[(2-furanylcarbonyl)oxy]-11[beta]-hydroxy-16α-methyl-3-oxo-androsta-1,4-diene-17β-carbothionate, (5)-(2-oxo-tetrahydro-furan-3S-yl)6α,9α-difluoro-11β-hydroxy-16α-methyl-3-oxo-17α-propionyloxy-androsta-1,4-diene-17β-carbothionate, and etiprednol-dichloroacetate (BNP-166), optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising flunisolide, beclomethasone, triamcinolone, budesonide, fluticasone, mometasone, ciclesonide, rofleponide, ST-126, dexamethasone, (S)-fluoromethyl 6α,9α-difluoro-1 Ia-[(2-furanylcarbonyl)oxy]-11β-hydroxy-16α-methyl-3-oxo-androsta-1,4-diene-17β-carbothionate, (S)-(2-oxo-tetrahydro-furan-3S-yl)6α,9α-difluoro-11β-hydroxy-16α-methyl-3-oxo-17α-propionyloxy-androsta-1,4-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

In particularly preferred medicament combinations the steroid 3 is selected from the group comprising budesonide, fluticasone, mometasone, ciclesonide, (S)-fluoromethyl 6α,9α-difluoro-1 Ia-[(2-furanylcarbonyl)oxy]-11β-hydroxy-16α-methyl-3-oxo-androsta-1,A-diene-17β-carbothionate, and etiprednol-dichloroacetate, optionally in the form of the racemates, enantiomers or diastereomers thereof and optionally in the form of the salts and derivatives thereof, the solvates and/or hydrates thereof.

Any reference to steroids 3 includes a reference to any salts or derivatives, hydrates or solvates thereof which may exist. Examples of possible salts and derivatives of the steroids 3 may be: alkali metal salts, such as for example sodium or potassium salts, sulphobenzoates, phosphates, isonicotinates, acetates, propionates, dihydrogen phosphates, palmitates, pivalates or furcates.

Optionally, the inhalation device according to the invention contains plural of doses of a medicament on powder form that contains beside one compound of formula 1 additionally both, one of the betamimetics 2 mentioned hereinbefore and one of the steroids 3 mentioned hereinbefore.

According to one aspect, there is provided an inhalation device according to the invention, wherein each blister contains a pharmaceutical composition in powder form wherein the pharmaceutical composition comprises one or more, preferably one, compound of formula 1.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised active substance I—, and optionally 2 and/or 3, preferably with an average particle size of 0.5 to 10 μm, more preferably from 1 to 6 μm, is added to the excipient mixture. Processes for producing the inhalable powders according to the invention by grinding and micronising and finally mixing the ingredients together are known from the prior art.

For the methods of preparing the pharmaceutical compositions in powder form reference may be made to the disclosure of WO 02/30390, WO 03/017970, or WO 03/017979 for example. The disclosure of WO 02/30390, WO 03/017970, and WO 03/017979 is hereby incorporated by reference into the instant patent application in its entirety.

As an example, the pharmaceutical compositions according to the invention may be obtained by the method described below.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

If after being chemically prepared the active substance used in the process described above is not already obtainable in a crystalline form with the particle sizes mentioned earlier, it can be ground up into the particle sizes which conform to the above-mentioned parameters (so-called micronising).

Many modifications and variations of the invention falling within the terms of the following claims will be apparent to those skilled in the art and the foregoing description should be regarded as a description of the preferred embodiments of the invention only.

Many modifications and variations of the invention falling within the terms of the following claims will be apparent to those skilled in the art and the foregoing description should be regarded as a description of the preferred embodiments of the invention only.

It will be appreciated that the inhalation device of the present invention may be used in conjunction with a spiral wound element and/or a fixed or flexible wall separating a chamber containing unused blisters from a chamber that receives the used blisters. Such modifications are known from the Applicant's own earlier European patent applications nos. 07111998.6 and 07111996.0.

The invention claimed is:

1. An inhaler comprising a housing to receive a strip having a plurality of blisters, each blister having a breachable lid and containing a dose of medicament for inhalation by a user, an indexing wheel mounted in the housing rotatable to drive a strip to sequentially move blisters into alignment with a blister piercing member, a control element pivotally mounted to the housing and a drive mechanism including a coupling member that rotates together with the control element, the coupling member being configured to couple the control element to the indexing wheel during part of the rotation of the control element by a user so that the indexing wheel rotates together with the control element;
wherein the indexing wheel is rotatably mounted to the coupling member and wherein the coupling member comprises an indexing wheel drive dog and the drive mechanism includes means to move, as the control element and coupling member are rotated, the indexing wheel drive dog into a position in which it cooperates with the indexing wheel so that the indexing wheel rotates together with the control element and the coupling member, wherein the coupling member includes a shaft having an axis coaxial with the axis of the control element, the indexing wheel being mounted on said shaft for rotation about said axis.

2. An inhaler according to claim 1, wherein the control element rotates relative to the housing about an axis and the coupling member is mounted for rotation about the same axis.

3. An inhaler according to claim 2, wherein the control element and coupling member are connected so that they rotate together.

4. An inhaler according to claim 1, wherein the coupling member is formed from a resilient material and said means for moving the indexing wheel drive dog into a position in which it cooperates with the indexing wheel moves said indexing wheel drive dog against a bias provided by said resilience.

5. An inhaler according to claim 4, wherein the coupling member comprises a flange that extends radially from one end of the shaft across one end of the indexing wheel.

6. An inhaler according to claim 5, wherein the flange lies in a plane extending substantially at right-angles to the axis of the shaft.

7. An inhaler according to claim 5, wherein the flange includes a flexible flange portion that resiliently bends or flexes relative to the remaining portion of the flange about an axis extending substantially at right angles to the axis of the shaft.

8. An inhaler according to claim 7, wherein the flange has an arcuate cut-out region configured such that the flexible flange portion is joined only to the remaining portion of the flange at each end.

9. An inhaler according to claim 8, wherein the flexible flange portion is hinged to the remaining portion of the flange at each end.

10. An inhaler according to claim 7, wherein the indexing wheel drive dog upstands from a surface of the flexible flange portion in a direction towards the indexing wheel.

11. An inhaler according to claim 10, wherein the means to move the indexing wheel drive dog into a position in which it cooperates with the indexing wheel so that the indexing wheel rotates together with the control element comprises a coupling member deflecting dog protruding from the flexible flange portion.

12. An inhaler according to claim 11, wherein the means to move the indexing wheel drive dog into a position in which it cooperates with the indexing wheel also comprises an arcuate guide track in the housing, the arcuate guide track having a first guide surface such that, when the coupling member is rotated in response to rotation of the control element in a first direction, the coupling member deflecting dog cooperates with the first guide surface to deflect the flexible flange portion towards the indexing wheel so that the indexing wheel drive dog cooperates with the indexing wheel to rotate the indexing wheel together with the coupling member.

13. An inhaler according to claim 12, wherein the arcuate guide track is configured such that the coupling member deflecting dog drops off the first guide surface prior to rotation of the control element to its maximum extent, the resilience of the flexible flange portion causing it to return to its original undeflected state so that the indexing wheel drive dog no longer cooperates with the indexing wheel, the indexing wheel now remaining stationary during continued rotation of the control element and coupling member to its maximum extent.

14. An inhaler according to claim 12, wherein the arcuate guide track comprises a second guide surface such that, when the flange portion deflecting dog has dropped off the first guide surface and the coupling member is rotated in response to rotation of the control element in a reverse direction, the flange portion deflecting dog cooperates with said second guide surface so that the flexible flange portion is deflected in the opposite direction, away from the indexing wheel.

15. An inhaler according to claim 14, wherein the coupling member deflecting dog comprises a first cooperating surface to engage the first guide surface of the arcuate guide track, and a second cooperating surface to engage the second guide surface of the arcuate guide track.

16. An inhaler according to claim 15, wherein the first and second guide surfaces of the arcuate guide track extend parallel to each other but spaced from each other in an axial direction.

17. An inhaler according to claim 16, wherein the first and second guide surfaces have angled end regions such that the coupling member deflecting dog rides up the angled end regions onto respective guide surfaces.

18. An inhaler according to claim 1, wherein the indexing wheel comprises a plurality of vanes and the indexing wheel drive dog contacts one of the vanes when the indexing wheel drive dog is moved into a position in which it cooperates with the indexing wheel so that the indexing wheel rotates together with the coupling member and the control element.

19. An inhaler according to claim 1, comprising a locking element to prevent rotation of the indexing wheel other than during cooperation of the indexing wheel drive dog with the indexing wheel.

20. An inhaler according to claim 19, wherein the locking element comprises a cantilevered arm mounted in the housing and having its free end biased against the indexing wheel, said free end of the cantilever arm cooperating with the indexing wheel so as to prevent rotation of the indexing wheel.

21. An inhaler according to claim 20, wherein the free end of the cantilevered arm is configured such that when the indexing wheel drive dog is moved towards the indexing wheel, further rotation of the coupling element causes the indexing wheel drive dog to engage the free end of the cantilever arm and deflect it out of locking engagement with the indexing wheel prior to cooperating with the indexing wheel to rotate the indexing wheel.

22. An inhaler according to claim 21, wherein the indexing wheel drive dog disengages the free end of the cantilever arm when the indexing wheel drive dog moves away from the indexing wheel so that the free end of the cantilever arm moves back towards the indexing wheel to lock the indexing wheel in position.

23. An inhaler according to claim 20, wherein the indexing wheel comprises a plurality of vanes and the free end of the cantilever arm comprises a slot, the slot being configured to receive a tip of a vane when the free end of the cantilever arm is biased against the indexing wheel to lock the indexing wheel in position.

24. An inhaler according to claim 23, wherein each vane comprises an enlarged head portion and the slot in the free end of the cantilever arm is configured to receive said enlarged head portion.

25. An inhaler according to claim 20, comprising a chassis to locate a blister strip as it moves therethrough, the cantilever arm extending from said chassis.

26. An inhaler according to claim 1, comprising a coiled strip of blisters received within the housing and passing around the indexing wheel.

* * * * *